United States Patent [19]

Abraham et al.

[11] 4,093,610
[45] June 6, 1978

[54] PROCESS FOR PRODUCING TRIGLYCYL-LYSINE VASOPRESSIN AND INTERMEDIATES THEREFOR

[75] Inventors: Nedumparambil A. Abraham, Dollard des Ormeaux; Hans U. Immer, Mount Royal; Kazimir Sestanj, Point Claire, all of Canada

[73] Assignee: American Home Products Corporation, New York, N.Y.

[21] Appl. No.: 763,772

[22] Filed: Jan. 31, 1977

[51] Int. Cl.² .................. C07C 103/52; C07G 7/00; C09H 00/00
[52] U.S. Cl. ................................. 260/112.5 R
[58] Field of Search ..................... 260/112.5 R

[56] References Cited

U.S. PATENT DOCUMENTS

| | | | |
|---|---|---|---|
| 3,232,923 | 2/1966 | Boissonnas et al. | 260/112.5 R |
| 3,299,036 | 1/1967 | Boissonnas et al. | 260/112.5 R |
| 3,371,080 | 2/1968 | Boissonnas et al. | 260/112.5 R |

FOREIGN PATENT DOCUMENTS

| | | | |
|---|---|---|---|
| 1,106,536 | 3/1968 | United Kingdom | 260/112.5 R |
| 927,714 | 6/1963 | United Kingdom | 260/112.5 R |

OTHER PUBLICATIONS

Kasofirek, et al., Coll. Czech. Chem. Commun., 31, 4581–4591, 1966.

*Primary Examiner*—Delbert R. Phillips
*Assistant Examiner*—Blondel Hazel
*Attorney, Agent, or Firm*—Stephen Venetianer

[57] ABSTRACT

A new process for preparing the cyclic dodecapeptide triglycyl-lysine vasopressin of the formula

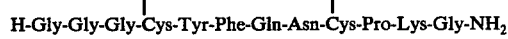

H-Gly-Gly-Gly-Cys-Tyr-Phe-Gln-Asn-Cys-Pro-Lys-Gly-NH₂ which comprises the preparation of a first hexapeptide of formula Boc—Gly—Gly—Gly—Cys(Trt)—Tyr—Phe—NHNH₂ and a second hexapeptide of formula H—Gln(Mbh)—Asn(Mbh)—Cys(Trt)—Pro—Lys(Boc)—Gly—NH₂ by a series of condensations involving the reaction of an appropriately protected peptide unit having an activated carboxyl with an appropriately protected peptide having a free amino group. Subsequently, the first and second hexapeptides are condensed according to the azide coupling method to obtain the linear protected dodecapeptide of formula Boc—Gly—Gly—Gly—Cys(Trt)—Tyr—Phe—Gln(Mbh)—Asn(Mbh)—Cys(Trt)—Pro—Lys(Boc)—Gly—NH₂; thereafter the linear protected dodecapeptide is transformed into the desired cyclic dodecapeptide, triglycyllysine vasopressin, by oxidizing and deprotecting processes.

12 Claims, No Drawings

PROCESS FOR PRODUCING TRIGLYCYL-LYSINE VASOPRESSIN AND INTERMEDIATES THEREFOR

BACKGROUND OF THE INVENTION a. Field of Invention

This invention relates to the cyclic dodecapeptide, triglycyl-lysine vasopressin or also called triglycyl-vasopressin, of the formula

More particularly this invention relates to an improved process for preparing triglycyl-lysine vasopressin and to intermediates used for the process.

b. Prior Art

The name "vasopressin" has been proposed for the factor found in pituitary extracts which controls the water balance as well as exhibiting other biological effects (see review by E. Schroder and K. Lübke in "The Peptides" Vol. 11, pp 336–358, Academic Press, New York and London, 1966).

A number of analogs of lysine vasopressin were prepared by E. Kasafirek et al, Coll. Czech. Chem. Commun., 31 4581(1966), most notably triglycyl-lysine vasopressin. Results from clinical trials by J. H. Cort et al, Europ. J. Clin. Invest., 5, 165–175(1975), show that this peptide has a prolonged effect on uterine contractions, thus useful for initiating abortive menstruation and in addition the peptide inhibits bleeding from both the gut and uterus.

The report relating to the synthesis of triglycyl-lysine vasopressin by Kasafirek et al, supra, does not give the experimental details for the preparation of the cyclic dodecapeptide. However, by analogy with the process used for the preparation of the other vasopressin analog in the same report, the over-all yield of the process for the vasopressin analog apparently is very low. In addition, it should be noted that the synthesis utilizes very stable protecting groups which require severe conditions for their removal.

In keeping with the need for a practical synthesis of the cyclic dodecapeptide, triglycyl-lysine vasopressin, the present invention discloses a new practical process for the large scale preparation of the cyclic dodecapeptide. Furthermore the present process has additional advantages in that it starts from readily available materials, avoids noxious reagents, is executed facilely, utilizes easily removable protecting groups and provides a pure product in high yield with a high degree of physiological potency.

SUMMARY OF THE INVENTION

According to the process of this invention the cyclic dodecapeptide, triglycyl-lysine vasopressin, of the formula

is prepared by transforming the protected linear dodecapeptide of formula Boc—Gly—Gly—Gly—Cys(Trt)—Tyr—Phe—Gln(Mbh)—Asn(Mbh)—Cys(Trt)—Pro—Lys(Boc)—Gly—NH₂ by oxidizing and deprotecting process steps.

In the preferred embodiment of the process of this invention the cyclic dodecapeptide, triglycyl-lysine vasopressin is prepared by oxidizing the protected linear dodecapeptide with iodine or thiocyanogen to obtain the protected cyclic disulfide dodecapeptide of formula

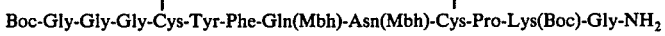

and subsequently removing all remaining protecting groups from the latter dodecapeptide under moderately acidic conditions.

In a further embodiment of the process of this invention the protected linear dodecapeptide is subjected to treatment with either mercuric acetate, mercuric chloride, silver acetate or silver nitrate to remove selectively the sulfhydryl protecting groups to obtain the corresponding mercuric or disilver salt of the corresponding disulfhydryl derivative; converting the salt to the protected disulfhydryl linear dodecapeptide by treatment with hydrogen sulfide, oxidizing said last-named dodecapeptide by treatment with oxygen, 1,2-diiodoethane, sodium or potassium ferricyanide, iodine or thiocyanogen to obtain the corresponding protected cyclic disulfide dodecapeptide and removing the remaining protecting groups under moderately acidic conditions to obtain the desired cyclic dodecapeptide.

The above described protected linear dodecapeptide is readily prepared by reacting according to the azide coupling method a first hexapeptide of formula Boc—Gly—Gly—Gly—Cys(Trt)—Tyr—Phe—NHNH₂ with a reagent, which furnishes nitrous acid in situ in the presence of a mineral acid, to convert the first hexapeptide to the corresponding first hexapeptide azide and reacting the azide with a second hexapeptide of formula H—Gln(Mbh)—Asn(Mbh)—Cys(Trt)—Pro—Lys(Boc)—Gly—NH₂.

DETAILS OF THE INVENTION

In general the abbreviations used herein for designating the amino acids and the protective groups are based on recommendations of the IUPAC-IUB Commission on Biochemical Nomenclature, see Biochemistry, II, 1726–1732 (1972). For instance, Gly, Cys, Tyr, Phe, Gln, Asn, Pro and Lys represent the "residues" of glycine, L-cysteine, L-tyrosine, L-phenylalanine, L-glutamine, L-asparagine, L-proline and L-lysine, respectively. The term "residue" means a radical derived from the corresponding L-amino acid by eliminating the OH portion of the carboxyl group and a H of the amino group. All the amino acids have the natural L-configuration.

A number of procedures or techniques for the preparation of peptides have hitherto been well established. For instance, the functional groups which are not involved in the peptide bond formation reaction are optionally protected by a protecting group or groups prior to the condensation reaction. For example, protecting groups which may be chosen for an amino function of a peptide or amino acid not involved in the peptide bond formation are; the alkoxycarbonyls which include benzyloxycarbonyl (represented by Z), t-butoxycarbonyl (represented by Boc), α,α-dimethyl-3,5-dimethoxy-benzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, or ethoxycarbonyl; the acyl type protecting groups which include formyl, trifluoroacetyl, phthalyl, acetyl (Ac), or toluenesulfonyl; the alkyl type protecting groups which include triphenylmethyl or trityl (represented by Trt) or benzyl; the preferred protecting groups and in the process of this invention are benzyloxycarbonyl, t-butoxycarbonyl, triphenylmethyl and α,α-dimethyl-3,5-dimethoxy-benzyloxycarbonyl. Although not essential, the hydroxy of tyrosine can be protected; protecting groups suitable for this purpose are represented by acetyl, tosyl, benzoyl, tert-butyl (represented by $Bu^t$), trityl, and benzyl (represented by Bzl); the preferred protecting group is benzyl. The protecting groups on the sulfur of cysteine or modified cysteine are illustrated by benzyl, triphenylmethyl or trityl (represented by Trt), benzyloxycarbonyl, or acetamidomethyl (represented by Acm); the preferred protecting group is trityl. The carboxylic acid function of a peptide or amino acid can be considered protected by a lower alkyl or lower aralkyl ester which include methyl (represented by OMe), ethyl (represented by OEt), or benzyl (represented by OBzl); and also by substituted hydrazides which include t-butoxycarbonyl hydrazide (represented by NHNH-Boc), benzyloxycarbonyl hydrazide (represented by NHNH-Z), or α,α-dimethyl-3,5-dimethoxy-benzyloxycarbonyl hydrazide (represented by NHNH-Ddz). In order to avoid undesirable side reactions the amide function on the side chain of the amino acid residue of glutamine and asparagine is protected with the 4,4-dimethoxybenzyhydryl group (represented by Mbh). The preparation and use of the latter protecting group is described by W. König and R. Geiger, Chem. Ber., 103, 2041(1070).

To promote facile condensation of the peptide carboxyl group with a free amino group of another peptide to form a new peptide bond the terminal carboxyl group must be activated. Descriptions of such carboxyl-activating groups are found in general textbooks of peptide chemistry; for example K. D. Kopple, "Peptides and Amino Acids", W. A. Benjamin, Inc., New York, 1966, pp. 45–51 and E. Schröder and K. Lübke, "The Peptides"; Vol. 1 Acedemic Press, New York, 1965, pp. 77–128. Examples of the activated form of the terminal carboxyl are acid chloride, anhydride, azide, activated ester, or o-acyl urea of a dialkylcarbodiimide. The following activated esters have proved to be particularly suitable in the process of this invention 2,4,5-trichlorophenyl (represented by OTcp), pentachlorphenyl (represented by OPcp), p-nitrophenyl (represented by ONp), or 1-benzotriazolyl; the succinimido (2,5-dioxo-1-pyrrolidinyl) group is also useful for such activation.

The term "azide method" as used herein refers to the method of coupling two peptide fragments which comprises the reaction of a peptide hydrazide with a reagent which furnishes nitrous acid in situ to obtain the corresponding azide and coupling the peptide azide with a peptide having a free amino group to obtain the desired peptide. Suitable reagents to form the azide from the hydrazide include organic nitrites (e.g. t-butyl nitrite or isoamyl nitrite) or alkali metal nitrite salts (e.g. sodium nitrite or potassium nitrite) in the presence of a mineral acid, preferably, hydrogen chloride, sulfuric acid phosphoric acid and the like. Preferred conditions for the azide method of coupling comprise reacting the peptide hydrazide with nitrous acid, generated in situ from an organic nitrite in the presence of a mineral acid, preferably hydrogen chloride, (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like or mixtures thereof, at −30° to 20° C, preferably at about −15° C for 10 to 30 minutes to obtain the corresponding azide. The peptide azide can be isolated and crystallized, if desired. However, the peptide azide is preferably allowed to remain in the reaction mixture. Thereafter the azide in the above mixture is reacted with the peptide unit having the free amino group at temperatures ranging from −30 to 20° C for about 1 to 2 hours and then at 0° to 30° C for 10 hours. An acid acceptor, preferably an organic proton acceptor, for example N-ethyldiisopropylamine, N-ethylmorpholine triethylamine and the like, is present in the reaction mixture in order to make the reaction medium slightly alkaline, preferably pH 7.0 to 7.5. See also the above cited textbooks of Kopple or Schroder and Lubke for additional descriptions of this method. The terms "peptide, tripeptide, hexapeptide, and the like" as used herein are not limited to refer to the respective parent peptide but are also used with reference to a peptide having functionalized or protecting groups. The term "peptide" as used herein is used with reference to a peptide with two to 12 amino acid residues.

The abbreviation Me represents a methyl group and $NHNH_2$ represents a hydrazide group.

The term "lower alkyl" as used herein contemplates hydrocarbon radicals having one to three carbon atoms and includes methyl, ethyl and propyl.

The term "mineral acid" as used herein contemplates the strong inorganic acids and includes hydrochloric, hydrobromic, sulfuric or phosphoric acid. When the term is used in conjunction with an anhydrous system, anhydrous hydrogen chloride is the preferred mineral acid.

The term "mildly acidic conditions" as used herein contemplates conditions in which a dilute aqueous solution of an organic acid, for example 5 to 20% aqueous formic, 50 to 100% aqueous acetic, 50 to 100% aqueous propionic acid, or mixtures thereof, is a principal component of the reaction medium.

The term "moderately acidic conditions" as used herein contemplates conditions in which concentrated organic acids or solutions of the mineral acids are used as a principal component of the reaction medium at temperatures ranging from about −30 to 30° C. Examples of preferred conditions in this case include the use of 50 to 100% trifluoroacetic acid at 0° to 30° C, 0.1 - 12N hydrochloric acid in aqueous solution or in solution in an organic solvent, or hydrogen chloride in solution in anhydrous organic solvents at −20° to 10° C.

The term "organic nitrite" includes the commercially available alkyl nitrites, for instance, t-butyl nitrite, isoamyl nitrite, and the like.

The term "organic proton acceptor" as used herein includes triethylamine, N-ethylmorpholine, N-ethyldiisopropylamine and the like.

The term "strong base" as used herein contemplates strong inorganic bases including the hydroxides and carbonates of sodium and potassium.

The cyclic dodecapeptide of this invention is obtained in the form of the free base or an acid addition salt either directly from the process of this invention or by reacting the peptide with one or more equivalents of the appropriate acid. Examples of preferred salts are those with pharmaceutically acceptable organic acids, e.g. acetic, lactic, succinic, benzoic salicyclic, methanesulfonic or toluenesulfonic acid; as well as polymeric acids such as tannic acid or carboxymethyl cellulose, and salts with inorganic acids such as hydrohalic acids, e.g. hydrochloric acid, or sulfuric acid, or phosphoric acid. It should be noted that the dodecapeptide has two basic nitrogens giving rise to addition salts with one to possible two equivalents of acid. If desired, a particular acid addition salt is converted into another acid addition salt, e.g., a salt with a non-toxic, pharmaceutically acceptable acid, by treatment with the appropriate ion exchange resin in the manner described by R. A. Boissonas et al., Helv. Chim. Acta, 43, 1349(1960). Suitable ion exchange resins are cellulose based cation exchangers, for example carboxy-methylcellulose or chemically modified, crosslinked dextran cation exchangers, for example, those of the Sephadex C type, and strongly basic anion exchange resins, for example those listed in J. P. Greenstein and M. Winitz "Chemistry of the Amino Acids", John Wiley and Sons, Inc., New York and London, 1962, Vol. 2, p. 1456.

The cyclic dodecapeptide of this invention forms complex salts with heavy metal ions. An example of a pharmaceuticaly acceptable heavy metal complex is a complex formed with zinc or with zinc protamine.

The cyclic dodecapeptide, triglycyl-lysine vasopressin, produced by the process of this invention, as well as the corresponding therapeutically acceptable salt, is useful because it possesses the same pharmacological activity as reported for triglycyl-lysine vasopressin by J. H. Cort et al., supra. The activity of the cyclic dodecapeptide is demonstrated readily in the pharmacological tests described by J. H. Cort et al, supra. For example, the cyclic dodecapeptide obtained by the process of this invention exhibits a prolonged haemostatic action and can be utilized to inhibit bleeding from peptic ulcers, gastrointestinal system, oesophageal varices and the uterus. The prolonged venonconstrictor action of the cyclic dodecapeptide is useful to reduce bleeding during surgery. In addition, the cyclic dodecapeptide increases tone as well as both rate and amplitude of uterine contractions for short periods in normal women just before the expected onset of menstruation. By initiating an abortive menstruation, the cyclic dodecapeptide can serve as a contraceptive.

When the cyclic dodecapeptide of this invention or a therapeutically acceptable salt thereof is employed in human medicine, it is administered systemically, either by intravenous, subcutaneous, or intramuscular injection, or by sublingual, nasal or vaginal administration, in compositions in conjunction with a pharmaceutically acceptable vehicle or carrier.

For administration by injection or by the nasal route as drops or spray, it is preferred to use the cyclic dodecapeptide in solution in a sterile aqueous vehicle which may also contain other solutes such as buffers or preservatives, as well as sufficient quantities of pharmaceutically acceptable salts or of glucose to make the solution isotonic.

The cyclic dodecapeptide produced by the process of this invention may also be administered as nasal or vaginal powders or insufflations. For such purposes the cyclic dodecapeptide is administered in finely divided solid form together with a pharmaceutically acceptable solid carrier, for example a finely divided polyethylene glycol ("Carbowax 1540"), finely divided lactose, or, preferably only for vaginal administration, very finely divided silica ("Cab-O-Sil"). Such compositions may also contain other excipients in finely divided solid form such as preservatives, buffers, or surface active agents.

For sublingual or vaginal administration it is preferred to formulate the cyclic dodecapeptide in solid dosage forms such as sublingual tablets or vaginal inserts or suppositories with sufficient quantities of solid excipients such as starch, lactose, certain types of clay, buffers, and lubricating, disintegrating, or surface-active agents, or with semi-solid excipients commonly used in the formulation of suppositories. Examples of such excipients are found in standard pharmaceutical texts, e.g. in Remington's Pharmaceutical Sciences, Mack Publishing Company, Easton, PA. 1970.

The dosage of the cyclic dodecapeptide obtained by the process of this invention will vary with the form of administration and with the particular patient under treatment. Generally, treatment is initiated with small dosages substantially less than the optimum dose of the hormone. Thereafter, the dosage is increased by small increments until the optimum effect under the circumstances is reached. In general, the cyclic dodecapeptide obtained by the process of this invention is most desirably administered at a concentration level that will generally afford the desired effect without causing any harmful or deleterious side effects, and preferably at a level that is in a range of from about 0.1 $\mu$g to about 100 $\mu$m per kilogram body weight per day, although as aforementioned variations will occur. However, a dosage level that is in the range of from about 0.5 $\mu$g to about 50 $\mu$g per kilogram body weight per day is most desirably employed in order to achieve effective results.

It is often desirable to administer the cyclic dodecapeptide continuously over prolonged periods of time in long-acting, slow-release, or depot dosage forms. such dosage forms may either contain a pharmaceutically acceptable salt of the hormone having a low degree of solubility in body fluids, for example one of those salts described below, or they may contain the cyclic dodecapeptide in the form of a water-soluble salt together with a protective carrier which prevents rapid release. In the latter case, for example, the cyclic dodecapeptide can be formulated with a non-antigenic partially hydrolyzed gelatin in the form of a viscous liquid; or the cyclic dodecapeptide can be adsorbed on a pharmaceutically acceptable solid carrier, for example zinc hydroxide, and may be administered in suspension in a pharmaceutically acceptable liquid vehicle; or the cyclic dodecapeptide can be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceuticaly acceptable liquid vehicles, preservatives, or sufactants. Examples of such formulations are found in standard pharmaceutical tests, e.g. in Remington's Pharmaceutical Sciences cited above. Long-acting, slow-release preparations of the cyclic dodecapeptide produced according to the process of this invention may also be obtained by microencapsulation in a pharmaceutically acceptable coating material, for example gelatine, polyvinyl alcohol or ethyl cellulose. Further examples of coating materials and of the processes used for microencapsulation are described by J. A. Herbig in "Encyclopedia of Chemical Technology", Vol. 13, 2nd. Ed., Wiley, New York 1967, pp. 436–456. Such formulations, as well as suspensions of salts of the cyclic dodecapeptide which are only sparingly soluble in body fluids, are designed to release from about 0.1 $\mu$g to about 50 $\mu$g of the cyclic dodecapeptide per kilogram body weight per day, and are preferably administered by intramuscular injection. Alternatively, some of the solid dosage forms listed above, for example certain sparingly water-soluble salts or dispersions in or adsorbates on solid carriers of salts of the cyclic dodecapeptide, for example dispersions in a neutral hydrogen of a polymer of ethylene glycol methacrylate or similar monomers cross-linked as desribed in U.S. Pat. No. 3,551,556 may also be formulated in the form of pellets releasing about the same amounts as shown above and may be implanted subcutaneously or intramuscularly.

Alternatively, slow-release effects over prolonged periods of time may also be obtained by administering the cyclic dodecapeptide obtained by the process of this invention in an intra-vaginal device or in a temporary implant, for example a container made of a non-irritating silicone polymer such as a polysiloxane, e.g. "Silastic", or of a neutral hydrogel of a polymer as described above, possessing the required degree of permeability ot release from about 0.1 $\mu$g to about 50 $\mu$g per kilogram body weight per day. Such intra-vaginal or implant dosage forms for prolonged administration have the advantage that they may be removed when it is desired to interrupt or to terminate treatment.

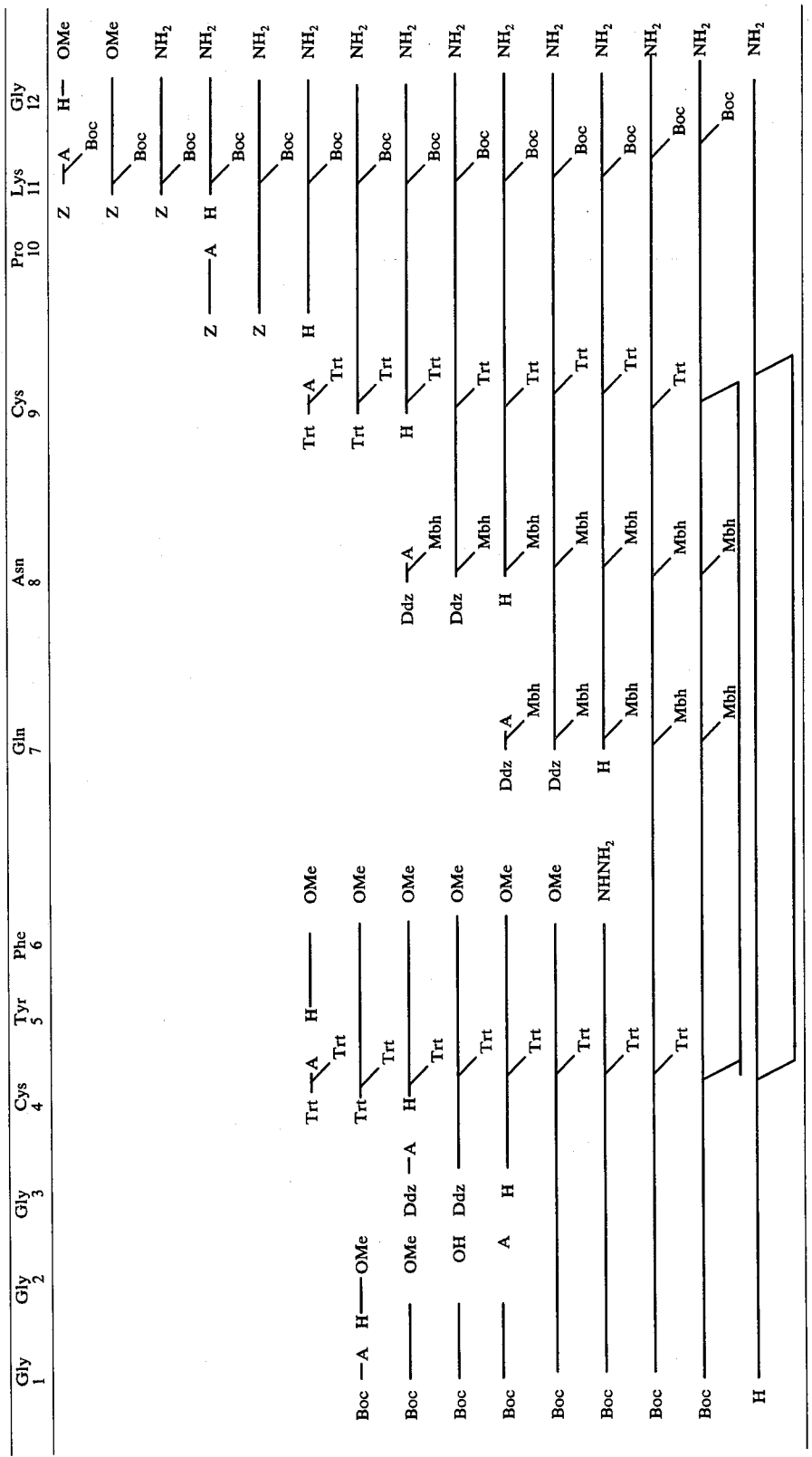
A = O-(carboxyl - activating group)

Process

The process of this invention is illustrated by the accompanying flow diagram of a preferred embodiment and the following description.

For convenience and clarity in the following discussion the individual peptide unit (i.e. amino acid) is sometimes designated by a number which has reference to the position in which the particular amino acid appears in the sequence of the amino acids as illustrated in the accompanying flow diagram.

First, with reference to the first hexapeptide (fragment 16 ) a practical and convenient preparation is realized by preparing a dipeptide (fragment 1-2 and a tetrapeptide (fragment 3-6) and subsequently coupling the latter two fragments.

More specifically, the fragment 1-2 is prepared by reacting an activated ester of Boc—Gly—OH with a lower alkyl ester of glycine, preferably H—Gly—OMe, to obtaining the corresponding lower alkyl ester of Boc—Gly—Gly—OH which in turn is hydrolyzed to afford its corresponding acid, Boc—Gly—Gly—OH. The latter dipeptide acid is then converted to a corresponding activated ester (fragment 1-2) for subsequent coupling with the fragment 3-6.

In a preferred embodiment the dipeptide fragment 1-2 is prepared by reacting t-hydroxybenzotriazole in an inert organic solvent, preferably dimethylformamide or tetrahydrofuran, in the presence of dicyclohexylcarbodimide (1.0 to 1.6 molar equivalents) at −20° to 10° C, preferably 0° C, for about 1 hour, then at 20° to 30° C for about 1 hour. In this manner for corresponding activated ester, i.e. the I-benzotriazolyl ester of Boc—Gly—OH, is formed in the solution. Without isolation the latter compound is then condensed with about one molar equivalent of glycine methyl ester hydrochloride in the presence of 1.0 to 1.5 molar equivalents of an organic proton acceptor (i.e., N-ethylmorpholine) in an inert organic solvent, preferably dimethylformamide, at 20° to 30° C for 10 to 24 hours to obtain Boc—Gly—Gly—OMe. The latter compound is now subjected to hydrolyzing to conditions to obtain the corresponding acid, Boc—Gly—Gly—OH. Preferred hydrolyzing conditions involve subjecting Boc—Gly—Gly—OMe to the action of a strong base, for example an excess of sodium or potassium hydroxide, in the presence of sufficient water to effect hydrolysis of the effect. The hydrolysis is preformed in an organic inert solvent, for example, metanol, ethanol or methoxyethanol. Under these conditions hydrolysis is usually completed within 1 to 3 hours at temperatures of 0° to 50° -C, preferably 20° to 30° C. Thereafter, Boc—Gly—Gly—OH is constructed to the corresponding activated ester, preferably Boc—Gly—Gly—OPcp (i.e. the desired dipeptide fragment 1-2) by condensing the latter acid with 1.1 to 2.0 molar equivalents of pentachlorophenol, in the presence 1.1 to 2.0 molar equivalents of dicyclohexylcarbodiimide in an inert organic solvent, for example dimethylformamide or tetrahydrofuran, at −20° to 20° C for 2 to 5 hours and then at 10° to 20° C for 15 to 24 hours.

With reference to the tetrapeptide fragment 3-6, the tetrapeptide is prepared by condensing an activated ester of N,S-ditrityl-cysteine (Trt—Cys(Trt)—OH) with a lower alkyl ester of tyrosyl-phenlalanine (H—Tyr—Phe—OH), preferably H—Tyr—Phe—OMe, preferably H—Tyr—Phe—OMe, to obtain the corresponding lower alkyl ester of N,S-ditrityl-cysteinyl-tyrosyl-phenylalanine (Trt—Cys(Trt)—Tyr—Phe—OH), preferably Trt—Cys(Trt)—Tyr—Phe—OMe; removing the terminal amino protecting group (Trt) from the latter compound under mildly acidic conditions to obtain the corresponding lower alkyl ester of (S-trityl)cysteinyl-tyrosyl-phenylalanine (H—Cys(Trt)—Try—Phe—OH), preferably H-Cys(Trt)—Tyr—Phe—OMe; condensing the latter compound with an activated ester of α,α-dimethyl-3,5-dimethoxybenzyloxycarbonyl-glycine (Ddz—Gly—OH) to obtain the corresponding lower alkyl ester of α,α-dimethyl-3,5-dimethoxybenzyloxycarbonyl-glycyl-(S-trityl)cysteinyl-tyrosyl-phenylalanine (Ddz—Gly—Cys(Trt)—Tyr—Phe—OH), preferably Ddz—Gly—Cys—(Trt)—Tyr—Phe—OMe; and removing the terminal amino protecting group-(Ddz) from the latter compound under mildly acidic conditions to obtain the corresponding lower alkyl ester of glycyl-(S-trityl)-cysteinyl-tyrosyl-phenylalanine (H—Gly—Cys(Trt)—Tyr—Phe—OH), preferably H—Gly—Cys(Trt)—Tyr—Phe—OMe, the desired tetrapeptide fragment 3-6.

In a preferred embodiment of the preparation of the above tetrapeptide fragment 3-6, the starting material N,S-ditritylcysteine 2,5-dioxo-1-pyrrolidinyl ester, described by B. Kamber et al., Helv., 53, 556(1970), is condensed with 1.0 to 1.4 molar equivalents of tyrosyl-phenylalanine methyl ester os the hydrobromide salt, described by R. L. Huguenin and S. Guttman, Helv., 48, 1885(1965), in the presence of an organic proton acceptor, preferably N-ethylmorpholine or triethylamine, in an inert organic solvent, preferably dimethylformamide, at 0° to 30° C for 3 to 6 days to obtain Trt—Cys(Trt)—Tyr—Phe—OMe.

Thereafter the latter compound is treated under mildly acidic conditons, preferably by dissolving the latter compound in acetic acid at 20° to 30° C and adding water until a solution of 70 to 90% acetic acid is obtained. The solution is stirred at 40° to 60° C for one to two hours and a further quantity of water is added. The precipitate is removed and the solvent in the filtrate is evaporated to give H—Cys—(Trt)—Tyr—Phe—OMe in the form of its acid addition salt with acetic acid. Although the latter salt can be converted to its corresponding free peptide by standard means, it is expedient to add the salt directly to the following condensation reaction mixture with a concomitant amount of an organic proton acceptor to compensate for the acid portion of the salt. In this manner the peptide as the free base exists in the solution. Indeed this latter consideration applies to all the deprotecting reactions of the present disclosure involving the removal of the protecting groups under moderately or mildly acidic conditions.

In the subsequent condensation reaction H—Cys(Trt)—Tyr—Phe—OMe in the form of its acetic acid addition salt is dissolved in dimethylformamide and the resulting solution is cooled to about 0° to 10° C. An excess, preferably 1.1 to 1.3 molar equivalents of an organic proton acceptor, preferably N-ethylmorpholine, is added to the solution; the solution now has a pH of about 8. Substantially one equivalent of α,α-dimethyl-3,5-dimethoxybenzyloxycarbonyl-glycine pentachlorophenyl ester (prepared from Ddz—Gly—OH and pentachlorophenol in the presence of dicyclohexylcarbodiimide) is added and the reaction mixture is kept at 20° to 30° C for 20 to 30 hours affording Ddz—Gly—Cys(Trt)—Tyr—Phe—OMe. Treatment of the latter tetrapeptide under mildly acidic conditions, preferably 60 to 90% acetic acid, at 20° to 30° C for 1 to 5 days gives the tetrapeptide H—Gly—Cys(Trt)—Tyr—Phe—OMe, the tetrapeptide fragment 3-6, in the form of its acetic acid addition salt.

The latter compound as the acetic addition salt is reacted with an organic proton acceptor to obtain H—Gly—Cys(Trt)—Tyr—Phe—OMe which is condensed with the aforementioned activated ester, Boc—Gly—Gly—OPcp (dipeptide fragment 1-2), to obtain Boc—Gly—Gly—Gly—Cys(Trt)—Tyr—Phe—OMe (hexapeptide fragment 1-6). Preferred conditions for this condensation include dissolving the acetic addition salt of the tetrapeptide and about 1.0 to 1.25 molar equivalents of Boc—Gly—Gly—OPcp in an inert organic solvent, preferably dimethylformamide, at 0° to 10° C and adding a sufficient amount of an organic proton acceptor, preferably N-ethylmorpholine, to keep the pH of the solution between 7 and 8. The resulting solution is kept at 10° to 30° C for 20 to 30 hours. Subsequently the hexapeptide ester, Boc—Gly—Gly—Gly—Cys(Trt)—Tyr—Phe—OMe, is isolated from the reaction mixture.

The latter compound is readily transformed to the corresponding first hexapeptide of this invention by reaction with an excess (20 to 50 molar equivalents) of hydrazine hydrate. Preferred conditions include treating the hexapeptide ester in an inert organic solvent, for example methanol or dimethylformamide, with 30 to 40 molar equivalents of hydrazine hydrate at 20° to 30° C for about 1 to 4 hours. Subsequent addition of water to the reaction mixture gives the desired first hexapeptide fragment 1-6 of formula Boc—Gly—Gly—Gly—Cys(Trt)—Tyr—Phe—NHNH$_2$.

A practical and convenient preparation for the second hexapeptide (fragment 7-12) comprises: condensing an activated ester of benzyloxycarbonyl-(N$^\epsilon$-t-butoxycarbonyl)lysine (Z—Lys(Boc)—OH) with a lower alkyl ester of glycine (H—Gly—OH) to obtain the lower alkyl ester of benzyloxycarbonal-(N$^\epsilon$-t-butoxycarbonyl)lysylglycine (Z—Lys(Boc)—Gly—OH), preferably Z—Lys(Boc)—Gly—OMe, reacting the latter compound with ammonia to obtain benzyloxycarbonyl-(N$^{3\,\epsilon}$-t-butoxycarbonyl)iysly-glycinamide (Z—Lys(Boc)—Gly—NH$_2$), removing the terminal amino protecting group from the latter compound using hydrogen in the presence of a noble metal catalyst to obtain (N$^\epsilon$-t-butoxycarbonyl)lysyl-glycinamide (H—Lys(Boc)—Gly—NH$_2$), condensing the latter compound with an activated ester of benzyloxycarbonylproline (Z—Pro—OH) to obtain benzyloxycarbonyl-prolyl-(N$^\epsilon$-t-butoxycarbonyl)lysyl-glycinamide (Z—Pro—Lys(Boc)—Gly—NH$_2$), removing the terminal amino protecting group (Z) from the latter compound using hydrogen in the presence of a noble metal catalyst to obtain prolyl-(N$^\epsilon$-t-butoxycarbonyl)lysyl-glycinamide (H-Pro-Lys(Boc)-Gly-NH$_2$), condensing the latter compound with an activated ester of N,S-ditrityl-cysteine to obtain N,S-ditrityl-cysteinyl-propyl-(N$^\epsilon$-t-butoxycarbonyl)lysylglycinamide (Trt—Cys(Trt)—Pro—Lys(Boc)—Gly—NH$_2$), removing the terminal amino protecting group (Trt) under mildly acidic conditions to obtain (S-trityl)cysteinyl-propyl-(N$^\epsilon$-t-butoxycarbonyl)lysyl-glycinamide (H—Cys(Trt)—Pro—Lys(Boc)—Gly—NH$_2$), condensing the latter compound with an activated ester of 3,5-dimethoxy-α,α-benzyloxycarbonyl-(N$^\Xi$-4,4'-dimethoxy-benzyhydryl)asparagine (Ddz—Asn(Mbh)—OH) to obtain 3,5-dimethoxy-α,α-dimethyl-benzyloxycarbonyl-(N$^\gamma$-4,4'-dimethoxy-benzyhydryl)asparaginyl-(S-trityl)cysteinly-prolyl-(N$^\epsilon$-t-butoxycarbonyl)lysyl-glycinamide (Ddz—Asn(Mbh)—Cys(Trt)—Pro-Lys(Boc)—Gly—NH$_2$), removing the terminal amino protecting group (Ddz) under mildly acidic conditions to obtain (N$^\gamma$-4,4'-dimethoxybenzyhydryl)asparaginyl-(S-trityl)-cysteinly-propyl-(N$^\gamma$-t-butoxycarbonyl)-lysyl-glycinamide (H—Asn(Mbh)—Cys(Trt)—Pro—Lys(Boc)—Gly—NH$_2$), condensing the latter compound with an activated ester of 3,5-dimethoxy-α,α-dimethyl-benzyloxycarbonyl-(N$^\delta$-4,4'-dimethoxybenzhydryl)glutamine (Ddz—Gln(Mbh)—OH) to obtain 3,5-dimethoxy-α,α-dimethyl-benzyloxycarbonyl-(N$^\delta$-4,4'-dimethoxybenzhydryl)glutaminyl-(N$^\gamma$-4,4'-dimethoxy-benzhydryl)asparaginyl-(s-trityl)cysteinyl-prolyl-(N$^\epsilon$-t-butoxycarbonyl)lysyl-glycinamide (Ddz—Gln(Mbh)—Asn(MbH)—Cys(Trt)—Pro—Lys(Boc)—Gly—NH$_2$) amino protecting group (Ddz) to obtain (N$^{\delta\text{-}4,4^1}$-dimethoxybenzhydryl)glutaminyl-(N$^{\gamma\text{-}4,4^1}$dimethoxy-benzhydryl)asparaginyl(S-trityl)cysteinyl-prolyl-(N$^\epsilon$-t-butoxycarbonyl)lysyl-glyciamide (H—Gln(Mbh)—Asn(Mbh)—Cys(Trt)—Pro—Lys(Boc)—Gly—NH$_2$), the second hexapeptide fragment 7-12.

In a preferred embodiment the second hexapeptide is prepared in the following manner.

With reference to the first step of the present embodiment, a solution of an activated ester of Z—Lys(Boc)—OH, preferably the p-nitrophenyl ester, and substantially one molar equivalent of a lower alkyl ester of glycine, preferably the methyl ester, in the presence of an organic proton acceptor (i.e. N-ethylmorpholine or triethylamine) in an inert organic solvent, for example ethyl acetate, tetrahydrofuran or dimethylformamide, at −5° to 10° C is prepared. The solution is kept at 20° to 30° C for 1 to 3 days and the lower alkyl ester of Z—Lys(Boc)—Gly—OH, preferably Z—Lys(Boc)—Gly—OMe, is isolated.

The latter compound is then reacted with a solution of 20 to 50 molar equivalents of ammonia in a lower alkanol, preferably methanol or ethanol, at −5° to 10° C for 20 to 30 hours. Evaporation of the solvents gives Z—Lys(Boc)—Gly—NH$_2$, dipeptide fragment 11-12.

Although the amide function is introduced into the latter dipeptide fragment at this point of the synthesis, the amide function can be introduced into any of the appropriate peptide fragments (i.e. tripeptide fragment 10-12, tetrapeptide fragment 9-12, pentapeptide fragment 8-12 or hexapeptide fragment 7-12) by retaining the terminal lower alkyl ester during the synthesis of these fragments and reacting the fragment with ammonia in the above manner.

The dipeptide, Z—Lys(Boc)—Gly—NH$_2$, is subjected to hydrogenation in the presence of a noble metal catalyst, i.e. 10% palladium on charcoal, and an equimolar amount of pyridine hydrochloride. Methanol, ethanol, acetic acid or mixtures thereof are convenient solvents for the hydrogenation. In this manner the terminal amino protecting group (Z) of the dipeptide is removed to give H—Lys(Boc)—Gly—NH$_2$, dipeptide fragment 11-12.

Coupling of the latter compound with an activated ester of Z—Pro—OH, preferably the p-nitrophenyl ester, in the same manner as described above gives Z—Pro—Lys(Boc)—Gly—NH$_2$, tripeptide fragment 10-12. Hydrogenation of the latter compound in the presence of a noble metal catalyst in the same manner as described above without using pyridine hydrochloride gives H—Pro—Lys(Boc)—Gly—NH₂, tripeptide fragment 10–12.

In the next step of the process, N,S-ditrityl-cysteine is converted to its corresponding activated ester, preferably the 1-benzotriazolyl ester, by reacting N,S-ditrityl-cysteine with 1.0 to 1.3 molar equivalents of 1-hydroxybenzotriazole and dicyclohexylcarbodiimide in an inert organic solvent, i.e. dimethylformamide, at −10° to 10° C for 1 to 3 hours and at 20° to 30° C for an additional hour. The latter mixture containing N,S-ditrityl-cysteine 1-benzotriazolyl ester is cooled to −10° to 5° C and a solution of an equimolar amount of H—Pro—Lys(Boc)—Gly—NH₂ and a sufficient amount of an organic acceptor, preferably N-ethylmorpholine, in an inert organic solvent, i.e. dimethylformamide, is added. The mixture is stirred at 20° to 30° C for 20 to 30 hours to obtain N,S-ditrityl-cysteinyl-prolyl-)Nᵉ-t-butoxycarbonyl)lysyl-glycinamide (Trt—Cys(Trt)—Pro—Lys(Boc)—Gly—NH₂), tetrapeptide fragment 9–12.

Treatment of the latter compound under mildly acidic conditions, preferably in a solution of 70 to 90% acetic acid at 35° to 60° C for 10 to 30 minutes, gives (S-trityl)cysteinyl-prolyl-(Nᵉ-t-butoxycarbonyl)lysyl-glycinamide (H—Cys(Trt)—Pro—Lys(Boc)—Gly—NH₂), as the acetate salt, tetrapeptide fragment 9–12.

An activated ester of 3,5-dimethoxy-α,α-dimethylbenzyloxycarbonyl-(Nᵞ-4,4′-dimethoxy-benzyhydryl)asparagine, preferably the 1-benzotriazolyl ester, is coupled with H—Cys(Trt)—Pro—Lys(Boc)—Gly—NH₂ in the same manner as described above to obtain 3,5-dimethoxy-α,α-dimethyl-benzyloxycarbonyl-(Nᵞ-4,4′-dimethoxy-benzhydry)asparaginyl-(S-trityl)cysteinly-prolyl-(Nᵉ-t-butoxycarbonyl)lysyl-glycinamide (Ddz—Asn(Mbh)—Cys(Trt)—Pro—Lys(Boc)—Gly—NH₂), pentapeptide fragment 8–12.

Removal of the amino protecting group (Ddz) from the latter compound under mildly acidic conditions, preferably in a solution of acetic acid-formic acid-water (7:1:2) at 20° to 30° C for 20 to 30 hours, gives (Nᵞ-4,4′-dimethoxy-benzhydryl)asparaginyl-(S-trityl)cysteinly-prolyl-(Nᵉ-t-butoxycarbonyl)lysyl-glycinamide (H—Asn(Mbh)—Cys(Trt)—Pro—Lys(Boc)—Gly—NH₂), pentapeptide fragment 8–12.

Repetition of the latter two reaction steps using an activated ester of 3,5-dimethoxy-α,α-dimethyl-benzyloxycarbonyl-(Nᵟ-4,4′-dimethoxy-benzhydryl)glutamine, preferably the 1-benzotriazolyl ester, and removing the amino protecting group (Ddz) from the formed Ddz—Gln(Mbh)—Asn(Mbh)—Cys(Trt)—Pro—Lys(Boc)—Gly—NH₂ gives (Nᵟ-4,4′-dimethoxy-benzhydryl)glutaminly-(Nᵞ-4,4¹-dimethoxy-benzhydryl)asparaginyl-(S-trityl)cysteinly-prolyl-(Nᵉ-t-butoxycarbonyl)lysyl-glycinamide (H—Gln(Mbh)—Asn(Mbh)—Cys(Trt)—Pro—Lys(Boc)—Gly—NH₂), the second hexapeptide fragment 7–12.

In the next step of the process of this invention the first hexapeptide (fragment 1-6) and the second hexapeptide (fragment 7-12) are coupled according to the azide coupling method to obtain the corresponding protected linear dodecapeptide of formula Boc—Gly—Gly—Gly—Cys(Trt)—Phe—Gln(Mbh)—Asn(Mbh)—Cys(Trt)—Pro—Lys(Boc)—Gly—NH₂.

A convenient and efficacious procedure for this step comprises dissolving the first hexapeptide hydrazide in dimethylformamide. A solution of about two to five molar equivalents, preferably three molar equivalents, of hydrogen chloride in ethyl acetate is added to the latter solution at −20° to 0° C, preferably −15° to 0° C. The mixture is cooled to −20° to −10° C, preferably −15° C, and t-butyl nitrate (1.0 to 1.5 molar equivalents, preferably 1.4 equivalents) is added to the stirred solution. After about 15 minutes at −20° to 10° C the mixture is rendered alkaline (pH 7–8) by the addition of an excess of an organic base, preferably 2 to 5 equivalents of N-ethyldiisopropylamine, to obtain a solution containing the hexapeptide azide, Boc—Gly—Gly—Gly—Cys(Trt)—Tyr—Phe—N₃. A solution of substantially one equivalent of the second hexapeptide in dimethylformamide is added to the solution containing the hexapeptide azide. A further addition of one to two equivalents of organic base can be made at this point in order to maintain a pH of about 7–8. The reaction mixture is then stirred at −10° to 0° C for 10 to 24 hours. Evaporation of the solvent, trituration of the residue with water, methanol or a mixture of methanol and aqueous citric acid (2 to 5%) and separation of the solid gives the aforementioned protected linear dodecapeptide.

A useful alternative synthesis of the protected linear dodecapeptide comprises: hydrolyzing the lower alkyl ester of the hexapeptide Boc—Gly—Gly—Gly—Cys(Trt)—Tyr—Phe—OH, preferably the methyl ester, with a strong base in the same manner as described above for the preparation of Boc—Gly—Gly—OH to obtain the first hexapeptide acid, Boc—Gly—Gly—Gly—Cys(Trt)—Tyr—Phe—OH; activating the terminal carboxyl of the latter peptide, preferably with an activated ester selected from those and in the same manner as described above; and coupling the latter carboxyl activated hexapeptide with the second hexapeptide of formula H—Gln(Mbh)—Asn(Mbh)—Cys(Trt)—Pro—Lys(Boc)—Gly—NH₂.

The conversion of the preceding protected linear dodecapeptide to triglycyl-lysine vasopressin is accomplished conveniently and efficiently by first oxidizing the protected linear dodecapeptide, preferably by the action of iodine in an inert solvent, i.e. a lower alkanol or acetic acid, whereby concomitant removal of the sulfhydryl protecting groups, i.e. Trt, and formation of the disulfide bridge occurs to give the corresponding protected cyclic disulfide dodecapeptide of formula

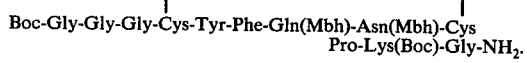
Boc-Gly-Gly-Gly-Cys-Tyr-Phe-Gln(Mbh)-Asn(Mbh)-Cys
Pro-Lys(Boc)-Gly-NH₂.

Subsequent treatment of the latter compound under moderately acidic conditions removes the remaining protecting groups (i.e. Mbh and Boc) to give triglycyl-lysine vasopressin.

In a preferred embodiment of the above transformation the protected linear dodecapeptide is dissolved in acetic acid or methanol, ethanol or other suitable lower alkanol, for example, propanol, isopropanol or butanol, preferably acetic acid. This solution is added to an excess of iodine (5 to 25, preferably 10 molar equivalents) dissolved in a lower alkanol, preferably 0.2 to 5% iodine in methanol. The time and temperature of this reaction is not critical; however, it is desirable to keep the reaction between 0° and 30° C by regulating the addition to the iodine solution or by cooling of the reaction mixture, or by a combination of both. Under these conditions the addition usually takes 30 to 60 minutes. After the addition of iodine the mixture is stirred at 20° to 30° C for 30 to 120 minutes, preferably for 60 minutes. Thereafter the mixture is cooled to about 0° C and an excess of a mild reducing agent, preferably sodium thiosulfate in aqueous solution, is added in order to destroy excess iodine. The mixture is concentrated and the residue is suspended in water. Collection of the solid material affords the desired protected cyclic disulfide dodecapeptide.

Alternatively, the protected linear dodecapeptide is converted to the aforementiond protected cyclic disulfide dodecapeptide by the method of R. G. Hiskey and R. L. Smith, J. Amer. Chem. Soc., 90, 2677 (1968) using thiocyanogen.

Again alternatively, the above protected cyclic disulfide dodecapeptide is also obtained by selectively removing the sulfhydryl protecting groups of the above protected linear dodecapeptide by the action of a mercuric or silver salt, for example, mercuric acetate, mercuric chloride, silver acetate or silver nitrate, in an inert organic solvent, for example dimethyformamide or acetic acid, according to known methods; for example, see B. Kamber, and W. Rittel, Helv. Chem. Soc. 87, 4922 (1965) and R. G. Denkewalter et al., J. Amer. Chem. Soc., 91, 502 (1969). The corresponding mercuric or disilver salt is then converted by hydrogen sulfide treatment to the protected linear disulfhydryl dodecapeptide of formula Boc—Gly—Gly—Gly—Cys—Tyr—Phe—Gln(Mbh)—Asn(Mbh)Cys—Pro—Lys(-Boc)—Gly—NH$_2$, see L. Zervas et al., cited above. The latter dodecapeptide is then converted to the aforementioned protected cyclic disulfide dodecapeptide by treatment with a mild oxidizing agent, for example iodine according to the method described hereinbefore, or oxygen according to the method of J. Rivier et al., C. R. Acad. Sci. Ser. D, 276, 2737 (1973), or 1,2-diiodoethane according to the method of F. Weygand and G. Zumach, Z. Naturforsch. 17b, 807 (1962), or sodium or potassium ferricyanide according to the method of D. Jarvis et al., J. Amer. Chem. oc., 83, 4780 (1961).

Finally, the aforementioned protected cyclic disulfide dodecapeptide is transformed into the cyclic dodecapeptide, triglycyl-lysine vasopressin, by subjecting the former to moderately acidic conditions whereby the remaining protecting groups of the protected cyclic disulfide dodecapeptide are removed. Examples of such moderately acidic conditions are 80 to 100% trifluoroacetic acid, 10 to 20% aqueous sulfuric acid, 10% phosphoric acid, 10 to 36% hydrochloric acid. In a preferred method to remove the remaining protecting groups, a solution of the protected cyclic disulfide dodecapeptide in a minimum of concentrated hydrochloric acid is rapidly stirred at −10° to 15° C for 5 to 30 minutes under a nitrogen atmosphere. Thereafter, glacial acetic acid (5 to 15 vols.) is added and the solution is lyophilized to give a residue of triglycyl-lysine vasopressin in the form of the hydrochloric acid addition salt.

In another preferred method to remove the remaining protecting groups from the protected cyclic disulfide dodecapeptide, a solution of the protected cyclic disulfide dodecapeptide in trifluoroacetic acid is stirred at −5° to 5° C for 0.5 to 1.5 hours and then at 20° to 30° C for 15 to 30 hours under a nitrogen atmosphere. The solution is evaporated under reduced pressure to give a residue of triglycyl-lysine vasopressin in the form of the trifluoroacetic acid addition salt. Any residual trifluoroacetic acid in the residue can be removed by dissolving the residue in a minimum of a lower alkanol and adding a di(lower)alkyl ether to obtain a precipitate of triglycyl-lysine vasopressin in the form of the trifluoroacetic acid addition salt.

The triglycyl-lysine vasopressin obtained after the treatment under moderately acidic conditions is purified further by ion exchange chromatography, preferably using carboxymethyl cellulose cation exchanger and ammonium acetate as the eluant. In this case the peptide is obtained in the form of its acid addition salt with acetic acid. Alternatively, the peptide is purified by partition chromatography on a chemically modified cross-linked dextran; for example, Sephadex LH-20 or Sephadex G-25. In the case where Sephadex LH-20 is employed and methanol as the eluting solvent, the peptide is obtained in the form of its acid addition salt corresponding to the acid under moderately acidic conditions, i.e. hydrochloric acid or trifluoroacetic acid. In the case where Sephadex G-25 and acetic acid or acetic acid-water-butanol is employed, the peptide is obtained in the form of its acetic acid addition salt. The latter salt, when subjected to repeated lyophilization from water yields the cyclic dodecapeptide triglycyl-lysine vasopressin for example the cyclic disulfide of glycyl-glycyl-glycly-cysteinyl-tyrosyl-phenylalanyl-glutaminyl-asparaginyl-cysteinyl-prolyl-lysyl-glycinamide, in the form of the free base.

Alternatively, the protecting groups (i.e. Trt, Mbh and Boc) are removed from the protected linear dodecapeptide by treatment under moderately acidic conditions, preferably concentrated hydrochloric acid or 100% trifluoroacetic acid as described above, to give the deprotected linear dodecapeptide of formula H—Gly—Gly—Gly—Cys—Try—Phe—Gln—Asn—Cys—Pro—Lys—Gly—NH$_2$. Subsequently, the latter dodecapeptide is oxidized with a mild oxidizing agent, for example iodine according to the method described hereinbefore or one of the other agents described above, to give the cyclic dodecapeptide, triglycyl-lysine vasopressin.

The following Examples illustrate further this invention.

EXAMPLE 1 t-Butoxycarbonyl-glycyl-glycine Pentachlorophenyl Ester, Boc—Gly—Gly—OPcp.

Dicyclohexylcarbodiimide (47.46 g, 0.23 mole) is added to a cooled (0° C), stirred solution of t-butoxycarbonyl-glycine (35.6 g, 0.2 mole) and 1-hydroxybenzotriazole (27.03 g, 0.2 mole) in dimethylformamide (400 ml). The mixture is stirred for 1 hour at 0° C and 1 hour at room temperature. A solution of glycine methyl ester hydrochloride (26.4 g, 0.21 mole) and N-ethylmorpholine (52.5 ml, pH 8) in dimethylformamide (1000 ml) is added to above mixture and the mixture is stirred overnight at room temperature. The mixture is filtered and the filtrate is evaporated. The residue is dissolved in ethyl acetate and the solution is washed with 10% citric acid (3×200 ml), saturated sodium bicarbonate (3×270 ml) and brine (2×135 ml), dried over anhydrous magnesium sulfate and evaporated to give t-butoxycarbonylglycyl-glycine methyl ester. To a cooled (0° C) solution of the latter compound (28.6 g, 0.12 mole) in methanol (200 ml) is added dropwise 1N sodium hydroxide (120 ml). The mixture is stirred for 2 hours at room temperature, cooled to 0° C and acidified with 50% citric acid to pH 4. The solution is evaporated to about one-half volume and the mixture is extracted with ethyl acetate. The organic extract is washed with water and brine, dried over anhydrous magnesium sulfate and evaporated. The residue is crystallized from ethyl acetate to give t-butoxycarbonyl-glycyl-glycine, mp 134°–136° C.

The latter compound (10.5 g, 0.045 mole) is dissolved in warm dimethylformamide (∼ 75 ml) and pentachlorophenyl (21.31 g, 0.08 mole) is added. The mixture is cooled to −5° C. Dicyclohexylcarbodiimide (16.51 g, 0.08 mole) in dimethylformamide (30 ml) is added dropwise. The stirring is continued for two hours at −5° C, 2 hours at 0° C and overnight at room temperature. The mixture is filtered and the filtrate is evaporated. The residue is dissolved in ethyl acetate and filtered. The filtrate is evaporated and the residue is crystallized from methanol to give the title compound, mp 168°–170° C.

EXAMPLE 2

N,S-Ditrityl-cysteinyl-tyrosyl-phenylalanine Methyl Ester, Trt—Cys(Trt)—Phe—OMe

N-Ethylmorpholine (9.9 g, 11 ml) is added to a solution of tyrosyl-phenylalanine methyl ester hydrobromide [31.6 g, 0.075 mole, described by R. L. Huguenin and S. Guttmann, Helv. 48, 1885(1965)] in dry distilled dimethylformamide (150 ml) under stirring and cooling at 0° C. N,S-Ditrityl-cysteine 2,5-dioxo-1-pyrrodidinyl ester [53.1 g, 0.068 mole, described by B. Kamber et al., Helv. 53, 556(1970)] is dissolved in dimethylformamide (170 ml) and the solution is cooled to 0° C and added to above reaction mixture. After stirring one day at 0° C, the mixture is warmed to room temperature and stirred for 4 days. The solvent is evaporated, the residue dissolved in ethyl acetate (1200 ml) and the precipitate is removed by filtration. The solution is washed with a citric acid solution (2.5%, 2×250 ml), saturated sodium bicarbonate (2×250 ml), saturated sodium chloride solution (250 ml) and dried over anhydrous magnesium sulfate. The solvent is evaporated and the residue is subjected to chromatography on silica gel using chloroform-methanol-pyridine (100:2:1). The appropriate eluant is evaporated to give the title compound nmr (CDCl$_3$) δ 3.41 (3H) and 6.2–8.0 (39H).

EXAMPLE 3

α,α-Dimethyl-3,5-dimethoxybenzyloxycarbonyl-glycyl-(S-trityl)cysteinyl-tyrosyl-phenylalanine Methyl Ester, Ddz—Gly—Cys(Trt)—Tyr—Phe—OMe Water (445 ml) is added dropwise to a solution of N,S-ditrityl-cysteinyl-tyrosyl-phenylalanine methyl ester (21.9 g, 23.5 mmoles, described in Example 1) in glacial acetic acid (1780 ml) at room temperature. The solution is stirred at 45° C for 1.5 hour and diluted with water (2200 ml). The precipitate is removed by filtration and the filtrate is evaporated. The last traces of acetic acid are removed by repeated evaporation with benzene to give (S-trityl)cysteinyl-tyrosyl-phenylalanine methyl ester.

The latter compound (16.3 g, 21.3 mmoles) and N-ethylmorpholine (9.7 g) are added to a solution at 0° C of α,α-dimethyl-3,5-dimethoxybenzyloxycarbonyl-glycine pentachlorophenyl ester (11.6 g, 21.3 mmoles, prepared from equal molar amounts of Ddz—Gly—OH, pentachlorophenol and dicyclohexylcarbodiimide) in dry distilled dimethylformamide (100 ml) After stirring for 19.5 hours at room temperature the reaction mixture is evaporated and the residue is dissolved in ethyl acetate (400 ml). The precipitate is removed by filtration and the filtrate is washed with 2.5% citric acid (3×100 ml), saturated sodium bicarbonate (3×100 ml) and brine (150 ml) and dried over anhydrous magnesium sulfate. The solvent is evaporated and the residue is crystallized from ethyl acetate/petroleum ether to give the title compound; mp 166°–169° C (dec.), $[\alpha]_D^{25}$ −4.1° (c=1, dimethylformamide).

EXAMPLE 4 t-Butoxycarbonyl-glycyl-glycyl-glycyl-(S-trityl)cysteinyl-tyrosylphenylalanine Methyl Ester, Boc—Gly—Gly—Gly—Cys(Trt)—Tyr—Phe—OMe The title compound of Example 3 (19.5 g, 10.9 mmoles) is dissolved in 80% acetic acid (1000 ml) and the solution is stirred for 3 days. The solution is evaporated. The residue is dissolved in methanol, the solvent is evaport is evaporated and the process is repeated with benzene. The residue is triturated with ether (i.e. diethyl ether) and dried to give glycyl(S-trityl)cysteinyltyrosyl-phenylalanine methyl ester as the acetate salt; mp 224°–228° C (dec.), $[\alpha]_D^{25}$ −3.67° (c = 1, dimethylformamide).

The latter compound as the acetate salt (7.25 g, 9.01 mmoles) is added to a stirring solution at 0° C of t-butoxycarbonyl-glycyl-glycine pentachlorophenyl ester (4.5, 9.46 mmoles, discribed in Example 1) in dry, distilled dimethylformamide (50 ml) and N-ethylmorpholine (1.04 g, 1.15 ml) is added. The reaction mixture is stirred at room temperature overnight. The solvent is evaporated to dryness and the residue is triturated with ether. The residue is crystallized from chloroform-ethanol to give the title compound; mp 211°–214° C and $[\alpha]_D^{25}$ −6.64° (c = 1, dimethylformamide).

EXAMPLE 5 t-Butoxycarbonyl-glycyl-glycyl-glycyl-(S-trityl)cysteinyl-tyrosylphenylalanine Hydrazide, Boc—Gly—Gly—Gly—Cys(Trt)—Tyr—Phe—NHNH$_2$ A solution of the title compound of Example 4 (1.8 g) and anhydrous hydrazine (2.16 ml) in dimethylformamide (10 ml) is stirred at 25° C for 2 hr. Water is added and the precipitate is collected. The precipitate is washed with water and dried to give the title compound, mp 200°–205° C (dec.).

EXAMPLE 6

Benzyloxycarbonyl-(N$^\epsilon$-t-butoxycarbonyl)lysyl-glycine Methyl Ester, Z—Lys(Boc)—Gly—OMe A solution of glycine methyl ester hydrochloride (1.25 g, 0.01 mole) in ethyl acetate (10 ml) and N-ethylmorpholine (1.28 ml) is added to a stirring solution at 0° C of benzyloxycarbonyl(N$^\epsilon$-butoxycarbonyl)lysine p-nitrophenyl ester (5.01 g, 0.01 mole) in ethyl acetate (20 ml). The reaction mixture is stirred at room temperature for 48 hr and filtered. The filtrate is washed with saturated sodium bicarbonate solution, saturated sodium chloride solution, 5% citric acid solution, saturated sodium chloride solution, saturated sodium bicarbonate solution, saturated sodium chloride solution and dried over sodium sulfate. After evaporation of the solvent, the residue is subjected to chromatography on silica gel using benzene-ethyl acetate-pyridine (60:40:1). The eluates are evaporated to give the title compound, nmr (CDCl$_3$) δ 1.42 (9H), 3.76 (3H), 5.2 (2H) and 7.4 (5H).

EXAMPLE 7

Benzyloxycarbonyl-(Nε-t-butoxycarbonyl)lysyl-glycinamide, z—Lys(Boc)—Gly—NH$_2$

A solution of the title compound of Example 6 (3.14 g) in methanol (10 ml) is added to 75 ml of methanol saturated with ammonia at 0° C. The mixture is allowed to stand at 5° C for 24 hr and evaporated. The residue is triturated with ether, dissolved in acetone and ether is added. The precipitate is collected and dried to give the title compound, nmr (CDCl$_3$) δ 1.4 (9H), 5.15 (2H) and 7.4 (5H).

EXAMPLE 8

Benzyloxycarbonyl-prolyl-(Nε-t-butoxycarbonyl)lysyl-glycinamide, Z—Pro—Lys(Boc)Gly—NH$_2$ A mixture of the title compound of Example 7 (2.68 )g, 0.00613 mole), pyridine hydrochloride ( 0.708 g, 0.00613 mole) and 10% palladium on carbon (0.46 g) in methanol (30 ml) is rapidly stirred under an atmosphere of hydrogen for 24 hr. The mixture is filtered and the filtrate is evaporated. The residue is dissolved in dimethylformamide (30 ml) and the solution is cooled to 0° C. N-Ethylmorpholine (0.78 g, 0.00613 mole) is added followed by benzyloxycarbonyl-proline p-nitrophenyl ester (2.39 g, 0.0065 mole). The reaction mixture is stirred at 0° to 5° C for 20 hr and evaporated. The residue is dissolved in ethyl acetate and filtered. The filtrate is washed with saturated sodium bicarbonate solution, saturated sodium chloride solution and dried over sodium sulfate. The solvent is evaporated and the residue is subjected to chromatography on silica gel using chloroform - methanol - triethylamine (100:5:1). The appropriate eluates are evaporated to give the title compound, $[\alpha]_D^{25}$ −32.5° (c = 1, dimethylformamide) and nmr (CDCl$_3$) δ 1.42 (9H), 5.2 (2H) and 7.4 (5H).

EXAMPLE 9

N,S-Ditrityl-cysteinyl-prolyl-(Nε-t-butoxycarbonyl)lysyl-glycinamide,
Trt—Cys(Trt)—Pro—Lys(Boc)—Gly—NH$_2$ A mixture of the title of Example 8 (2.3 g, 0.0043 mole) and 5% palladium on carbon (0.24 g) in acetic acid (36 ml) is stirred rapidly under an atmosphere of hydrogen until the hydrogen ceases to be absorbed. The mixture is filtered and the filtrate is evaporated to give prolyl-(Nε-t-butoxycarbonyl)lysyl-glycinamide as the acetate salt.

A solution of N,S-ditrityl-cysteine [prepared from N,S-ditrityl-cysteine diethylamine salt (3.86, 0.0057 mole)], 1-hydroxybenzotriazole (0.918 g, 0.0068 mole) and dicyclohexylcarbodiimide (1.174 g, 0.0057 mole) in dimethylformamide (25 ml) is stirred at 0° C for 2 hr and at room temperature for one hr. The mixture is cooled to 0° C and a solution of prolyl-(Nε-t-butoxycarbonyl)lysyl-glycinamide acetate (prepared above) and N-ethylmorpholine (0.55 ml) in dimethylformamide (30 ml) is added. The mixture is stirred for 20 hr at 25° C and filtered. The filtrate is evaporated and the residue is dissolved in ethyl acetate. After filtering, the filtrate is washed with 2.5% citric acid solution, saturated sodium bicarbonate solution and saturated sodium chloride solution, dried over sodium sulfate and evaporated. The residue is subjected to chromatography on silica gel using chloroform-methanol-triethylamine (100:4:1). The appropriate eluates are evaporated to give the title compound.

EXAMPLE 10

3,5-Dimethoxy-α,α-dimethyl-benzyloxycarbonyl-(Nγ-4,4'-dimethoxybenzhydryl)asparaginyl-(S-trityl)cysteinyl-prolyl-(Nε-t-butoxycarbonyl)lysyl-glycinamide,
Ddz—Asn(Mbh)—Cys(Trt)—Pro—Lys(Boc)—Gly—NH$_2$ A solution of the title compound of Example 9 (6.0 g, 0.00608 mole) in acetic acid-water (4:1, 50 ml) is stirred at 45° C for 15 min and cooled to 25° C. Water (40 ml) is added and the mixture is filtered. The filtrated is evaporated to give (S-trityl)cysteinyl-prolyl-(Nε-t-butoxycarbonyl)lysylglycinamide as the acetate salt.

A solution of 3,5-dimethoxy-α,α-dimethyl-benzyloxycarbonyl-(Nγ-4,4'-dimethoxy-benzhydryl)-asparagine [3.34 g, 0.00575 mole, described by C. Birr Liebigs Ann. Chem., 1973, 1652)], 1-hydroxybenzotriazole (1.44 g, 0.0107 mole) and dicyclohexylcarbodiimide (2.83 g, 0.0137 mole) in dimethylformamide (20 ml) is stirred at 0° C for one hr and at 25° C for 2 hu and cooled to 0° C. The mixture is added to a solution of (S-trityl)cysteinyl-propyl(Nε-t-butoxycarbonyl) lysyl-glycinamide acetate (prepared above) in dimethylformamide (20 ml) and the resulting mixture is stirred at 0° C for 2 hr and at 25° C for 20 hr. The precipitate is removed and the filtrate is evaporated. The residue is dissolved in ethyl acetate and filtered. The filtrate is washed with 2.5% citric acid solution, saturated sodium chloride solution, saturated sodium bicarbonate solution and saturated sodium chloride solution, dried over sodium sulfate and evaporated. The residue is subjected to chromatography on silica gel using methanolchloroform-triethylamine (5:95:0.1). The appropriate eluates are evaporated to give the title compound, $[\alpha]_D^{25}$ −23.8 (c =1, chloroform) and amino acid analysis: Lys (1.01), Cys (0.95), Asp (1.01), Pro(0.99) and Gly (1.00).

EXAMPLE 11

3,5-Dimethoxy-α,α-dimethyl-benzyloxycarbonyl-(Nγ-4,4'-dimethoxy-benzhydryl)glutainyl-(Nγ-4,4'-dimethoxy-benzhydryl)asparaginyl-(S-trityl)cysteinylprolyl-(Nγ-t-butoxycarbonyl)lysyl-glycinamide,
Ddz—Gln(Mbh)—Asn(Mbh)—Cys(Trt)—Pro—Lys(Boc)—Gly—NH$_2$ The title compound of Example 10 (2.5 g, 0.0019 mmole) in acetic acid-formic acid-water (7:1:2) is stirred at 25° C for 20 hr and evaporated. The residue is dissolved in methanol, dilute ammonium hydroxide is added until pH 9 is obtained, water is added and the solution is extracted with chloroform. The organic extract is washed with sodium bicarbonate solution, dried over magnesium sulfate and evaporated. The residue is subjected to chromatography on silica gel using chlorofom-methanoltriethylamine (100:5:0.1) and the appropriate eluates are evaporated to give (Nγ-4,4'-dimethoxy-benzhydryl)asparaginyl-(S-trityl)cysteinylprolyl-(Nε-t-butoxycarbonyl)lysyl-glycinamide.

A solution of 3,5-dimethoxy-α,α-dimethyl-benzyoxycarbonyl (Nδ-4,4'-dimethoxy-benzhydryl)-glutamine[1.12 g, 0.00189 mole, described by C. Birr Liebigs Ann. Chem., 1973, 1652], 1-hydroxybenzotriazole (0.508 g, 0.0038 mole) and dicyclohexylcarbodiimide(0.777 g, 0.0038 mole) in dimethylformamide (9 ml) is stirred at −10° C for 30 min, at 25° C for 2 hr and cooled to −10° C. A solution of (N<sup>γ</sup>-4,4'-dimethoxybenzhydryl)asparaginyl-(S-trityl)cysteinyl-prolyl-(N<sup>ε</sup>-t-butoxycarbonyl)lysylglycinamide (prepared above) in dimethylformamide (18.6 ml) is added to the latter solution and the reaction mixture is stirred at 25° C for 24 hr. After cooling to 0° C, sodium bicarbonate (1.0 g) is added and the reaction mixture is stirred at 25° C for 20 min. The mixture is filtered and the filtrate is evaporated. The residue is dissolved in ethyl acetate and filtered. The filtrate is washed with sodium bicarbonate solution, dried over sodium sulfate and evaporated. The residue is subjected to chromatography on silica gel using chloroform-methanoltriethylamine (90:10:0.1) and the appropriate eluates are evaporated to give the title compound; $[\alpha]_D^{25}$ − 25.2° (c = 1, chloroform) and amino acid analysis: Lys(1.02), Glu(0.96), Cys(0.91), Pro(0.96), Asp(1.02) and Gly(1.00).

EXAMPLE 12

(N<sup>δ</sup>-4,4'-Dimethoxy-benzhydryl)glutaminyl-(N<sup>γ</sup>-4,4'-dimethoxy-benzhydryl)asparaginyl-(S-trityl)cysteinyl-prolyl-(N<sup>ε</sup>-t-butoxycarbonyl)lysylglycinamide, H—Gln(Mbh)—Asn(Mbh)—CYs(Trt)—Pro—Lys(-Boc)—Gly—NH<sub>2</sub>

A solution of the title compound of Example 11 (3.6 g) in acetic acid-formic acid-water (7:1:2, 39 ml) is stirred at 25° C for 20 hr and evaporated. The residue is dissolved in chloroform and the solution is washed with saturated sodium bicarbonate solution and water, dried over sodium sulfate and evaporated. The residue is subjected to chromatography on silica gel using chloroform-methanoltriethylamine (95:5:0.1) and the appropriate eluates are evaporated to give the title compound, mp 120°–145° C.

EXAMPLE 13 t-Butoxycarbonyl-glycyl-glycyl-glycyl-(S-trityl)cysteinyl-tyrosylphenylalanyl-(N<sup>δ</sup>-4,4'-dimethoxy-benzhydryl)glutaminyl-(N<sup>γ</sup>4,4'-dimethoxy-benzhydryl)asparaginyl-(S-trityl)cysteinyl-propyl-(N<sup>ε</sup>-t-butoxycarbonyl)lysyl-glycinamide, Boc—Gly-Gly-Gly-Cys(Trt)—Tyr—Phe—Gln(Mbh)—Asn(Mbh)—Cys(Trt)—Pro—Lys(Boc)—Gly—NH<sub>2</sub>

A solution of the title compound of Example 5 (0.80 g, 0.883 mmole) in dimethylformamide (5 ml) is cooled to −20° C and anhydrous hydrogen chloride in ethyl acetate (4.7 N, 0.45 ml, 2.08 mmole) is added followed by t-butyl nitrite (0.115 ml, 1.0 mmole). The solution is stirred at −15° C for 15 min and N-ethyldiisopropylamine (0.37 ml, 2.08 mmole) is added followed by a solution of the title compound of Example 12 (1.25 g, 0.87 mmole) in dimethylformamide (2 ml). The reaction mixture is stirred at −15° C for 1 hr, at 0° C for 1 hu and at 25° C for 20 hr. The mixture is evaporated and the redidue is triturated with methanol to give the title compound, mp 210° C(dec.) and amino acid analysis: Lys(0.92), Cys(1.84), Asp(0.92), Glu(0.92), Pro(1.24), Gly(4.0), Tyr(0.64) and Phe(1.00).

EXAMPLE 14

Cyclic Disulfide of t-Butoxycarbonyl-glycyl-glcyl-cysteinyl-tyrosyl-phenylalanyl-(N<sup>δ</sup>-4,4<sup>1</sup>-dimethoxyl-benzhydryl)glutaminyl-(N<sup>γ</sup>-4,4<sup>1</sup>-dimethoxy-benzhydryl)asparaginyl-cysteinyl-prolyl-(N<sup>ε</sup>-t-butoxycarbonyl)lysyl-glycinamide,Boc-Gly-Gly-Gly-Cys- Tyr-Phe-Gln-(Mbh)-Asn-(Mbh)-Cys-Pro-Lys(Boc)-Gly-NH<sub>2</sub>

The title compound of Example 13 (2.75 g) is dissolved in hot glacial acetic acid (182 ml). The solution is cooled to 25° C and added dropwise within one hr to a 0.5% solution of iodine in methanol (570 ml). The mixture is stirred at 25° C for 1.5 hr, cooled to 0° C and an aqueous solution of sodium thiosulfate (IN, 22 ml) is added. The mixture is evaporated and the residue is dissolved in methanol. Water is added and the precipitate is collected and dried to give the title compound, mp 150°–158° C.

EXAMPLE 15

Cyclic Disulfide of Glycyl-glycyl-glycyl-cysteinyl-tyrosyl-phenylalanyl-glutaminyl-asparaginyl-cysteinyl-prolyl-lysyl-glycinamide, H-Gly-Gly-Gly-Cys-Tyr-Phe-Gln-Asn-Cys-Pro-Lys-Gly-NH<sub>2</sub>

A solution of the title compound of Example 14 (2.885 g) in trifluoroacetic acid (28.8 ml) and anisole (2.88 ml) is stirred at 0° C for one hr and at 25° C for 20 hr. The solution is evaporated and the residue is dissolved in methanol. Isopropyl ether is added and the precipitate is collected. The precipitate is subjected to chromatography on carboxymethyl cellulose (Whatman CM-23) using 0.01 M ammonium acetate buffer followed by evaporation of the appropriate eluates. The residue is lyophilized to give the title compound as the acetate salt, $[\alpha]_D^{27}$ − 82.2° (c = 0.17, 0.5% acetic acid). The latter salt is lyophilized from water (three times) to give the title compound as the free base, amino acid analysis: Gly(4.0), Cys(1.92), Try(1.00), Phe(1.08), Glu(1.00), Asp(0.96), Pro(1.00) and Lys(1.24).

We claim:

1. A process for preparing a cyclic dodecapeptide of the formula

H-Gly-Gly-Gly-Cys-Tyr-Phe-Gln-Asn-Cys-Pro-Lys-Gly-NH<sub>2</sub> which comprises the steps of:
reacting first hexapeptide of formula Boc—Gly—Gly—Gly—Cys(Trt)—Tyr—Phe—NHNH<sub>2</sub> with a reagent which furnishes nitrous acid in situ in the presence of a mineral acid to convert said first hexapeptide to the corresponding first hexapeptide azide and reacting said azide with a second hexapeptide of formula H—Gln(Mbh)—Asn(Mbh)—Cys(Trt)—Pro—Lys(Boc)—Gly—NH<sub>2</sub>
oxidizing the resulting protected linear dodecapeptide of the formula:

Boc—Gly—Gly—Gly—Cys(Trt)—Tyr—Phe—Gln(Mbh)—Asn(Mbh)—Cys(Trt)—Pro—Lys(Boc)—Tly—NH<sub>2</sub> with iodine or thiocyanogen to obtain the protected cyclic disulfide dodecapeptide of the formula

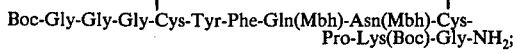

reacting said protected linear dodecapeptide with mercuric acetate, mercuric chloride, silver acetate of silver nitrate to obtain the corresponding mercuric or disilver salt of the corresponding disulfhydryl derivative, reacting said salt with hydrogen sulfide to obtain the protected linear disulfhydryl dodecapeptide, oxidizing said last-named dodecapeptide with oxygen, 1,2-diiodoethane, sodium or potassium ferricyanide, iodine or thiocyanogen to obtain said protected cyclic disulfide dodecapeptide;] and deprotecting said protected cyclic disulfide dodecapeptide in the presence of a concentrated organic acid or an aqueous solution of a mineral acid under moderately acidic conditions appropriate to remove the Boc and Mbh protecting groups to obtain said cyclic dodecapeptide.

2. A process as claimed in claim 1 wherein said protected linear dodecapeptide is oxidized with a solution of iodine in a lower alkanol and/or acetic acid at 0° to 30° C for 30 to 180 minutes.

3. A process as claimed in claim 1 wherein said protected cyclic disulfide dodecapeptide is deprotected with a solution of trifluoroacetic acid at −5° to 30° C for 10 to 30 hours.

4. A process as claimed in claim 1 wherein said protected cyclic disulfide dodecapeptide is deprotected with a solution of concentrated hydrochloric acid at −10° to 15° C for 5 to 30 minutes.

5. A process as claimed in claim 1, wherein said first hexapeptide is prepared by reacting an activated ester of Trt—Cys(Trt)—OH with a lower alkyl ester of H—Tyr—Phe—OH to obtain a lower alkyl ester of Trt—Cys(TrT)—Tyr—Phe—OH, removing the terminal amino protecting group from said last-named compound under mildly acidic conditions to obtain a lower alkyl ester of H—Cys(TrT)—Tyr—Phe—OH, reacting said last-named compound with an activated ester of Ddz—Gly—OH to obtain a lower alkyl ester of Ddz—Gly—Cys(Trt)—Tyr—Phe—OH, removing the terminal amino protecting group from said last-named compund under mildly acidic conditions to obtain a lower alkyl ester of H—Gly—Cys(Trt)—Tyr—Phe—OH, reacting said last-named compound with an activated ester of Boc—Gly—Gly—OH to obtain a lower alkyl ester of Boc—Gly—Gly—Gly—Cys(Trt)—Tyr—Phe—OH and reacting said last-named compound with hydrazine hydrate.

6. A process as claimed in claim 1, wherein said second hexapeptide is prepared by condensing an activated ester of Z—Lys(Boc)—OH with a lower alkyl ester of H—Gly—OH to obtain a lower alkyl ester of Z—Lys(Boc)—Gly—OH, recating said last-named compound with ammonia to obtain Z—Lys(Boc—Gly—NH₂, hydrogenating said last-named compound in the presence of a noble metal catalyst to obtain H—Lys(Boc)—Gly—NH₂, condensing said last-named compound with an activated ester of Z—Pro—OH to obtain Z—Pro—Lys(Boc)—Gly—NH₂, hydrogenating said last-named compound in the presence of a noble metal catalyst to obtain H—Pro—Lys(Boc)—Gly—NH₂, condensing said last-named compound with an activated ester of Trt—Cys(Trt)—OH to obtain Trt—Cys(Trt)—Pro—Lys(Boc)—Gly—NH₂, removing the terminal amino protecting group from said last-named compound under mildly acidic conditions to obtain H—Cys(Trt)—Pro—Lys(Boc)—Gly—NH₂, condensing said last-named compound with an activated ester of Ddz—Asn(Mbh)—OH to obtain Ddz—Asn(Mbh)—Cys(Trt)—Pro—Lys(Boc)—Gly—NH₂, removing the terminal amino protecting group from sad last-named compound under mildly acidic conditions to obtain H—Asn(Mbh)—Cys(Trt)—Pro—Lys(Boc)—Gly—NH₂, condensing said last-named compound with an activated esterof Ddz—Gln(Mbh)—OH to obtain Ddz—Gln(Mbh)—Asn(Mbh)—Cys(Trt)—Pro—Lys(Boc)—Gly—NH₂, and removing the terminal amino protecting group from said last-named compound under mildly acidic conditions to obtain said second hexapeptide.

7. A process for preparing a cyclic dodecapeptide of the formula

which comprises the steps of:
reacting a first hexapeptide of formula Boc—Gly—Gly—Gly—Cys(Trt)—Tyr-Phe—NHNH₂ with a reagent which furnishes nitrous acid in situ in the presence of a mineral acid to convert said first hexapeptide to the corresponding first hexapeptide azide and reacting said azide with a second hexapeptide of formula H—Gln(Mbh)—Asn(Mbh)—Cys(Trt)—Pro—Lys(Boc)—Gly—NH₂— reacting, resulting the protected linear dodecapeptide of the formula Boc—Gly—Gly—Gly—Cys(Trt)—Tyr—Phe—Gln(Mbh)—Asn(Mbh)—Cys(Trt)—Pro—Lys(Boc)—Gly—NH₂ with mercuric acetate, mercuric chloride, silver acetate or silver nitrate to obtain the corresponding said salt with hydrogen sulfide to obtain the protected inear disulfhydryl dodecapetide; oxidizing said last-named dodecapeptide with oxygen, 1,2-diiodoethane, sodium or potassium ferricyanide, iodine or thiocyanogen to obtain the protected cyclic disulfide dodecapeptide of the formula

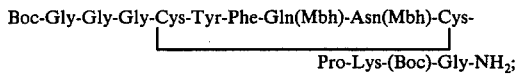

and deprotecting said protected cyclic disulfide dodecapeptide in the presence of a concentrated organic acid or aqueous solution of mineral acid under moderately acidic conditions appropriate to remove the Boc and Mbh protecting groups to obtain the said cyclic dodecapeptide.

8. The compound of the formula Boc—Gly—Gly—Gly—Cys(Trt)—Tyr—Phe—OMe.

9. The compound of the formula Boc—Gly—Gly—Gly—Cys(Trt)—Tyr—Phe—NHNH₂.

10. The compound of the formula Boc—Gly—Gly—Gly—Cys(Trt)—Tyr—Phe—Bin(Mbh)—Msn(Mbh)—Cys(Trt)—Pro—Lys(Boc)—Gly—NH₂.

11. The compound of the formula

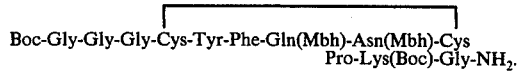

12. The compound of the formula H—Gln(Mbh)—Asn(Mbh)—Cys(Trt)—Pro—Lys(Boc)—Gly—NH₂.